US00PP22325P2

(12) United States Plant Patent
Talmadge

(10) Patent No.: US PP22,325 P2
(45) Date of Patent: Dec. 13, 2011

(54) ***IPOMOEA* PLANT NAMED 'IPOSGBRO'**

(50) Latin Name: *Ipomoea batatas*
Varietal Denomination: IPOSGBRO

(75) Inventor: Paul Talmadge, Orcutt, CA (US)

(73) Assignee: Floranova Service Corp

( * ) Notice: Subject to any disclaimer, the term of this patent is extended or adjusted under 35 U.S.C. 154(b) by 0 days.

(21) Appl. No.: 12/807,425

(22) Filed: Sep. 2, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette Para
(74) *Attorney, Agent, or Firm* — Cassandra Bright

(57) ABSTRACT

A new and distinct *Ipomoea batatas* cultivar named 'IPOSGBRO' is disclosed, characterized by light green and red palmate shaped foliage, and a bush forming, habit. Additionally the new cultivar flowers under long day conditions and produces many lateral branches, without pinching or chemical growth regulators. The new cultivar is an *Ipomoea batatas*, typically suited for ornamental container and garden use.

1 Drawing Sheet

Figure 1:
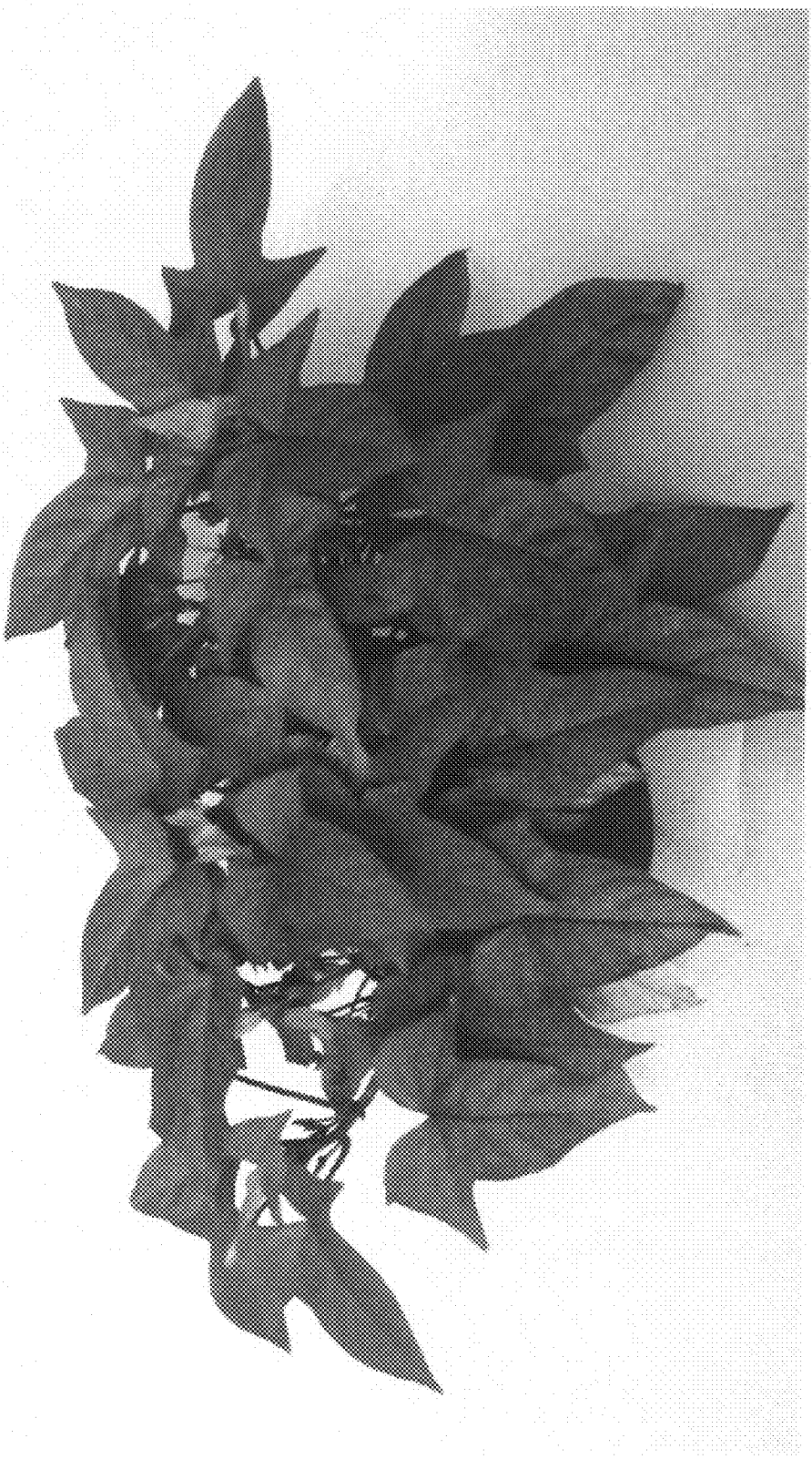

Latin name of the genus and species: *Ipomoea batatas:*
Variety denomination: 'IPOSGBRO'.

BACKGROUND OF THE INVENTION

The new variety originated from a commercial breeding program under the direction of the inventor, Paul A. Talmadge. The crossing resulting in the new cultivar was made in Fall of 2007, with the seed parent, an unpatented, unnamed proprietary seedling and the pollen parent, also an unpatented, unnamed proprietary seedling. The new variety was discovered by the inventor in April of 2008 at a commercial greenhouse in Lompoc, Calif.

After selecting and isolating the new cultivar, asexual reproduction of the new cultivar 'IPOSGBRO' was first performed in a commercial research greenhouse in Lompoc, Calif. during June of 2008. 'IPOSGBRO' has since produced several generations and has shown that the unique features of this cultivar are stable and reproduced true to type. Asexual reproduction of the new variety is by vegetative cuttings.

SUMMARY OF THE INVENTION

The cultivar 'IPOSGBRO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IPOSGBRO.' These characteristics in combination distinguish 'IPOSGBRO' as a new and distinct *Ipomoea* cultivar:

1. Bush forming plant habit
2. Unique foliage color an intermediate between light green and red.
3. Long day flowering.
4. Average to large foliage size.
5. Very well branched, without pinching or chemical growth regulator use.

PARENTAL COMPARISON

Plants of the new cultivar 'IPOSGBRO' are similar to the seed parent in most horticultural characteristics. However, 'IPOSGBRO' differs in producing palmate, rather than cordate shaped foliage. Additionally the seed parent has completely light green colored foliage, short day flowering, and a vining, poorly branched plant habit.

Plants of the new cultivar 'IPOSGBRO' are similar to the pollen parent in most horticultural characteristics. However, 'IPOSGBRO' produces green-red colored foliage, whereas the pollen parent has dark purple foliage. Additionally the pollen parent has smaller leaves than 'IPOSGBRO.'

COMMERCIAL COMPARISON

Plants of the new cultivar 'IPOSGBRO' are best compared to the commercial variety *Ipomoea batatas* 'Sweet Caroline Bronze' U.S. Plant Pat. No. 15,437. Plants of 'IPOSGBRO' are similar to plants of 'Sweet Caroline Bronze' in most horticultural characteristics, however, plants of 'IPOSGBRO' form a bush shape, with many short, secondary lateral branches, whereas 'Sweet Caroline Bronze' will develop a vining, trailing habit with age, and requires pinching to develop lateral branches. Additionally 'IPOSGBRO' flowers under long day conditions, whereas 'Sweet Caroline Bronze' is short day flowering.

BRIEF DESCRIPTION OF THE PHOTOGRAPH

The accompanying photograph in FIG. 1 illustrates in full color a typical plant of 'IPOSGBRO' grown in a greenhouse in Lompoc, Calif. This plant is approximately 8 weeks old, from an unrooted cutting, shown in a 6 inch pot pot. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Formula Guide Solid Matte, First Edition 2000-2001, except where general terms of ordinary dictionary significance are used. The following observations and measurements describe 'IPOSGBRO' plants grown during the Summer months in a greenhouse in Lompoc, Calif., under bright, unshaded conditions. Average day temperatures were approximately 26° C. and the average night temperature was approximately 18° C. No artificial light, photoperiodic treatments or chemical treatments were given to the plants. Measurements and numerical values represent averages of typical plant types.

Botanical classification: *Ipomoea batatas* 'IPOSGBRO'

Age of the plant described: Approximately 8 weeks from an unrooted cutting.

Container size of the plant described: 6 inch commercial container.

PROPAGATION

*Propagation method.*—Terminal cuttings.

*Time to develop roots suitable for transplanting.*—Summer — about 6 days at an average temperature of 24° C.; Winter-about 10 days at an average temperature of 24° C.

*Root description.*—Thick, fleshy.

*Tuber description.*—None observed.

PLANT

*Growth habit.*—Compact, upright and mounding.

*Height.*—Measured from top of soil line of pot, approximately 22 cm.

*Plant spread.*—Approximately 50 cm.

*Growth rate.*—Rapid.

*Branching characteristics.*—Very free branching, alternate occurring.

Primary lateral branches:

*Length.*—A range between 19-24 cm.

*Diameter.*—Approximately 0.6 cm.

*Texture.*—Glabrous, with occasional hairs seen with a hand lens.

*Color.*—Near Pantone 505C.

*Strength.*—Strong.

*Internode length.*—A range between 0.5-1.0 cm.

*Adventitious roots at nodes.*—Not observed.

Secondary lateral branches:

*Length.*—Ranging from 2-4 cm.

*Diameter.*—Approximately 0.3 to 0.4 cm.

*Texture.*—Glabrous, with occasional hairs seen with a hand lens.

*Color.*—Near Pantone 505C at base, gradually changing to Pantone 384C at tip.

*Strength.*—Pliable.

*Internode length.*—Range between 0.4 to 0.6 cm.

*Quantity per 8 week old plant.*—Approximately 18.

*Adventitious roots at nodes.*—None observed.

New shoot growth characteristics:

*Color.*—Pantone 384C.

*Aspect.*—Upright.

*Texture.*—Glabrous.

FOLIAGE

Leaf:

*Arrangement.*—Alternate, simple.

*Average length.*—Approximately 13 cm.

*Average width.*—Approximately 11-12 cm.

*Shape of blade.*—3 lobed palmate.

*Apex.*—Acuminate.

*Base.*—Cordate to auriculate.

*Margin.*—Entire, with tiny hairs visible with a hand lens.

*Aspect.*—Folded upwards slightly along midrib at base, flattening to curving downward toward apex.

*Texture of top surface.*—Glabrous.

*Texture of bottom surface.*—Glabrous.

*Quantity of leaves per lateral branch.*—Approximately 11.

Color:

*Young foliage upper side.*—Pantone 384C.

*Young foliage under side.*—Pantone 384C.

*Mature foliage upper side.*—Pantone 385C with a vibrant sheen of Pantone 505C giving the overall impression of Pantone 491C.

*Mature foliage under side.*—75% Pantone 505C, mottled with 25% Pantone 384C.

Venation:

*Type.*—Palmate: arcuate to reticulate.

*Venation color upper side.*—Pantone 505C.

*Venation color under side.*—Pantone 505C.

Petiole:

*Length.*—A range from approximately 11-13 cm.

*Diameter.*—Approximately 0.4 cm at base, 0.3 cm at top.

*Texture.*—Mostly glabrous with a few hairs visible with a hand lens.

*Color.*—Pantone 505C.

*Strength.*—Strong.

*Aspect.*—Upright to slightly curved.

FLOWER

Bloom period: Blooms continuously under 13 hour, or longer, photo period

Inflorescence:

*Arrangement.*—Single axillary peduncle with buds attached in a cluster at the top.

*Type.*—Cyme.

*Height.*—Approximately 13 cm.

*Width.*—Approximately 4.5 cm.

*Quantity of flowers per inflorescence.*—3-7 buds, only one open flower at a time.

Bud:

*Bud shape.*—Slightly twisted ovate with a pointed tip.

*Bud length.*—Approximately 1.8 cm.

*Bud diameter.*—Approximately 0.5 cm.

*Bud color.*—Pantone 451C.

*Calyx color.*—Pantone 506C.

Individual flower:

*Shape.*—Funnel form.

*Quantity of flowers per plant.*—2 observed open.

*Quantity of buds per plant.*—Approximately 75.

*Diameter of entire flower.*—Approximately 4.5 cm.

*Depth of flower.*—Approximately 3.5 cm.

*Rate of opening.*—Fully open 1 day from bud stage.

*Flower longevity on plant.*—1 day.

*Self cleaning.*—Spent flower drops off easily.

*Fragrance.*—None.

Petals:

*Petals fused.*—Funnel form, slightly 5 lobed.

*Petal texture.*—Outside of funnel glabrous; flattened open top of funnel glabrous: lower interior of funnel has many hairs.

Color:

*Outer surface of funnel.*—Pantone 524C.

*Flattened open top of funnel.*—Pantone 517C.

*Interior of funnel.*—Pantone 517C with numerous vertical stripes of Pantone 513C gradually denser towards bottom.

SEPAL

*Number.*—5.
*Sepal appearance.*—Sepals fully enclose very young buds. Bud grows beyond sepals 1 cm prior to opening.
*Sepal arrangement.*—Overlapping.
*Sepal length.*—Approximately 0.8 cm.
*Sepal width.*—Approximately 0.3 cm.
*Sepal shape.*—Oblong.
*Base.*—Attached smoothly with acute edges.
*Apex shape.*—Acuminate to aristate.
*Margin.*—Entire.
*Color.*—Pantone 506C.

PEDUNCLE

*Present.*—Yes.
*Length.*—Approximately: 5-7 cm.
*Diameter.*—Approximately 0.2-0.3 cm.
*Angle.*—Upright.
*Strength.*—Strong.
*Color.*—Pantone 506C.

OTHER CHARACTERISTICS

Seeds and fruits: No seeds/fruits observed.
Disease/pest resistance: Neither resistance nor susceptibility to the normal pests and diseases of *Ipomoea* has been observed.
Temperature tolerance: Tolerates low temperatures to approximately 2° C. Good high temperature tolerance, observed to at least 40° C.

What is claimed is:

1. A new and distinct cultivar of *Ipomoea batatas* plant named 'IPOSGBRO' as herein illustrated and described.

* * * * *